US006960223B1

(12) United States Patent
Ambach

(10) Patent No.: US 6,960,223 B1
(45) Date of Patent: Nov. 1, 2005

(54) TOURNIQUET DEVICE FOR SINGLE-HANDED OPERATION

(75) Inventor: Robert Ambach, 1112 First St. #176, Coronado, CA (US) 92118

(73) Assignee: Robert Ambach, Oceanside, CA (US)

( * ) Notice: Subject to any disclaimer, the term of this patent is extended or adjusted under 35 U.S.C. 154(b) by 531 days.

(21) Appl. No.: 10/125,808

(22) Filed: Apr. 18, 2002

(51) Int. Cl.7 .......................................... A61B 17/132
(52) U.S. Cl. ..................................................... 606/203
(58) Field of Search ............................... 606/201, 203; 24/32, 298; 128/99.1, 105.1; 2/311–342

(56) References Cited

U.S. PATENT DOCUMENTS

| | | | | |
|---|---|---|---|---|
| 1,317,319 | A | * | 9/1919 | Robinson ..................... 606/203 |
| 1,322,050 | A | * | 11/1919 | Plummer ..................... 606/203 |
| 4,125,115 | A | | 11/1978 | Mayo et al. |
| 4,243,039 | A | * | 1/1981 | Aginsky ..................... 606/203 |
| 4,516,576 | A | | 5/1985 | Kirchner |
| 4,640,281 | A | | 2/1987 | Sturm et al. |

* cited by examiner

Primary Examiner—Julian W. Woo
Assistant Examiner—Sarah Webb
(74) Attorney, Agent, or Firm—Black Lowe & Graham PLLC

(57) ABSTRACT

A first belt extends between and through two opposing slip buckles which allow the belt to be pulled freely through them but only in respective directions which shorten the belt segment between the buckles. Each slip buckle includes a release which when operated allows the belt to slip freely through said each buckle in either direction. A second belt is affixed at one end to one of the slip buckles, the other end being connected to a mechanism by which a user can spool the second belt to selectively shorten its free length. The spooling mechanism is coupled to the other slip buckle, preferably by means of a fixed length belt, to complete a tourniquet loop. Preferably the spooling mechanism includes a rachet mechanism operated by a lever in a pumping manner. Preferably the loop can be opened and closed.

9 Claims, 6 Drawing Sheets

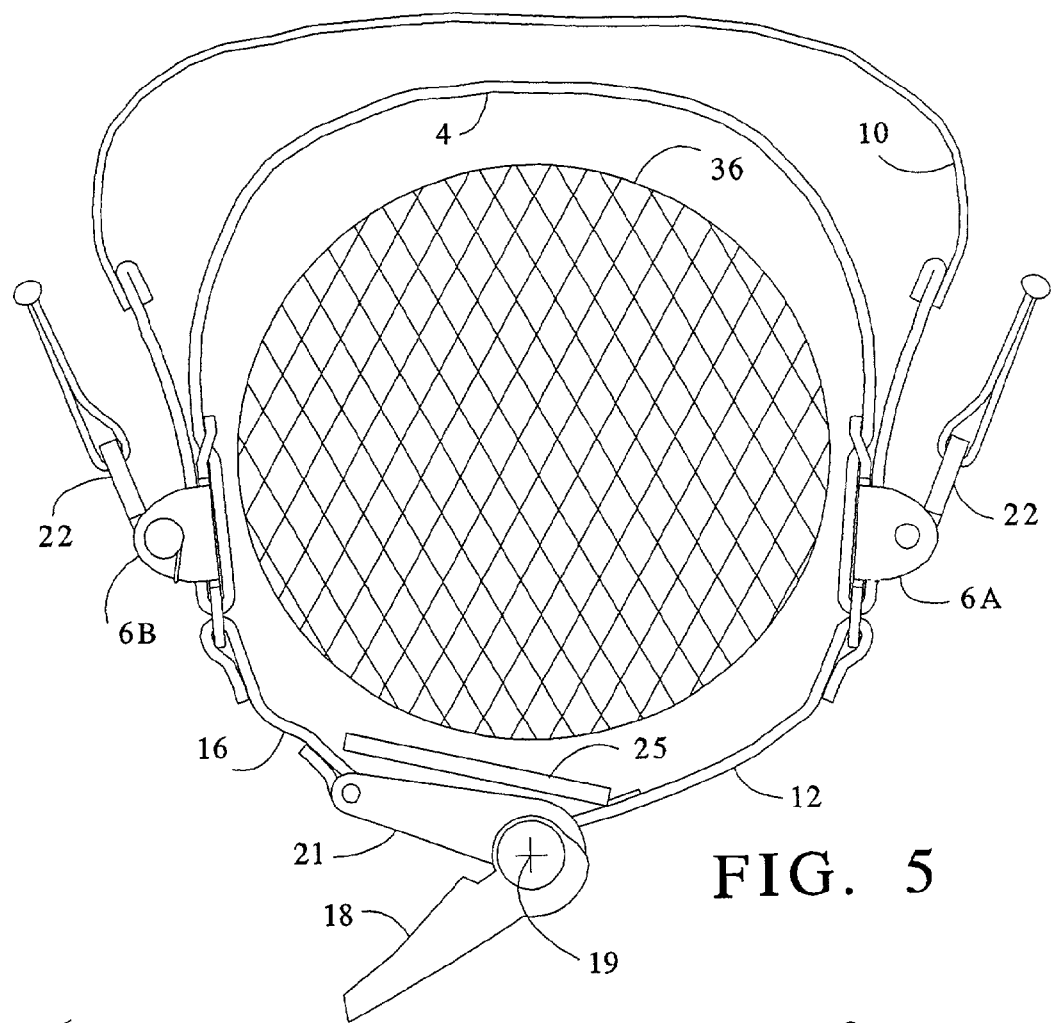
FIG. 5
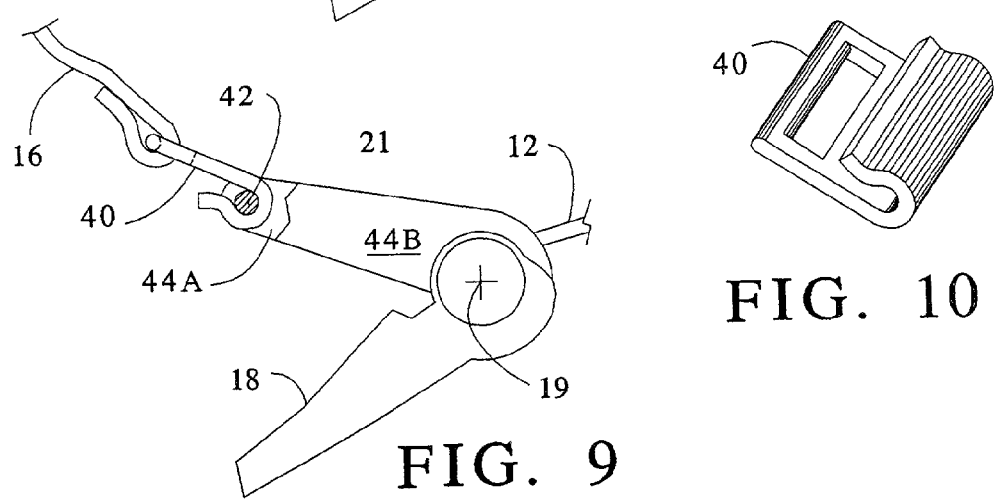
FIG. 9
FIG. 10

TOURNIQUET DEVICE FOR SINGLE-HANDED OPERATION

BACKGROUND OF THE INVENTION

This invention relates in general to the field of tourniquets and more particularly to a tourniquet device which can be operated with just one hand.

Tourniquets are well known for the purpose of temporarily restricting the flow of blood to a person's injured limb in order to prevent a serious loss of blood. If a person's arm is injured to the extent that significant blood is being lost, another person can generally fashion a tourniquet from available materials, such as a belt, rope, cord, or cloth, and apply it to the injured arm to restrict or stop the bleeding, allowing time to seek medical attention. However, when such an injury occurs where assistance is unavailable and the injured arm is incapacitated or severed, it is difficult if not impossible for the injured person to effectively apply a tourniquet to the injured arm, and depending on the rate of blood loss, the injured person may have only a very short time to stop the bleeding in order to survive. While the need for being able to self-apply a tourniquet to one's injured arm has existed through the ages, heretofore there has not been an effective solution.

The tourniquet device of this invention addresses this problem and provides a solution, providing a tourniquet which can be effectively and quickly applied single-handedly, i.e. using only one hand if necessary. With this invention a person having a seriously injured arm can apply a tourniquet to the injured arm and tighten it with his free (uninjured) hand. This invention can actually be used to quickly and easily apply a tourniquet to any limb, not just an arm, and can of course be applied using two hands, but it is tremendously advantageous in all situations in which only one hand is available to apply a tourniquet. For example, a person with only one usable arm can apply this invention to another person's bleeding limb, especially in situations where the other person is either unconscious or otherwise unable to assist.

Other advantages and attributes of this invention will be readily discernable upon a reading of the text hereinafter.

SUMMARY OF THE INVENTION

An object of this invention is to provide a tourniquet device for restricting the flow of blood in a person's limb.

An additional object of this invention is to provide a tourniquet device that can easily be applied using just one hand.

A further object of this invention is to provide a tourniquet device that can be self-applied using only one hand.

These objects, and other objects discernable from a study of this document, are accomplished by a tourniquet loop adapted for single-handed operation comprising: a first loop segment being single-handedly adjustable in length for coarsely tightening the loop around a limb; and a second loop segment being single-handedly adjustable in length for further tightening the loop enough to at least restrict blood flow in the limb. Preferably the tourniquet loop can be opened and closed as needed. In a preferred embodiment, the first tourniquet loop segment includes two opposing slip buckles; a first belt extending between and through the slip buckles, each slip buckle allowing the belt to be pulled freely through it in a direction which shortens the length of first belt between the slip buckles but preventing the first belt from traversing through it in the opposite direction; and a line means, grippable by a single hand, for pulling the first belt through the slip buckles in respective directions which shorten the length of first belt between the slip buckles. Preferably at least one slip buckle further includes a release which when selectively actuated allows the first belt to be pulled through said at least one slip buckle in either direction. Also in a preferred embodiment, the second tourniquet loop segment comprises a second belt affixed at one end to one slip buckle; a belt tightening mechanism, engaged with the other end of the second belt, by which a user can selectively shorten the length of second belt between the mechanism and said one slip buckle; and a coupling between the mechanism and the other slip buckle to complete the tourniquet loop. One embodiment of the belt tightening mechanism includes a rotatable spool onto which the second belt can be spooled; a lever by which the spool is turned in the direction of spooling the second belt; and a rachet mechanism for allowing the spool to turn in the direction of spooling the second belt but preventing it from turning in the opposite direction. One embodiment of a slip buckle includes a base; a cylinder rotatable on an axis lateral to the first belt, the cylinder including a ridged eccentricity, the cylinder axis being so disposed in fixed relation to the base that the eccentricity can be rotated to impinge upon the first belt which extends between the base and the cylinder and when so rotated the eccentricity seizing and wedging the first belt against the base whenever the first belt is pulled oppositely to the direction which shortens the length of first belt between the slip buckles; and a bias which urges the cylinder to assume an angular disposition at which the eccentricity impinges upon the belt. Also preferably a slip buckle further includes a lever by which a user can rotate the cylinder against the bias to release the first belt. and a release for allowing the second belt to be unspooled.

BRIEF DESCRIPTION OF THE DRAWINGS

FIG. 5 is the first of four plan views illustrating operation of the invention. In this view, the invention has been loosely slipped over a person's injured arm represented in diamond hatched cross-section.

FIG. 9 is a partial plan view illustrating an alternative embodiment in which the tourniquet loop can be selectively opened to facilitate application, and then re-closed to tighten it around a limb.

FIG. 10 is a pictorial view of a hook clasp, as illustrated in FIG. 9, useable to selectively open and close the tourniquet loop.

DESCRIPTION OF THE PREFERRED EMBODIMENT

Figure 1:
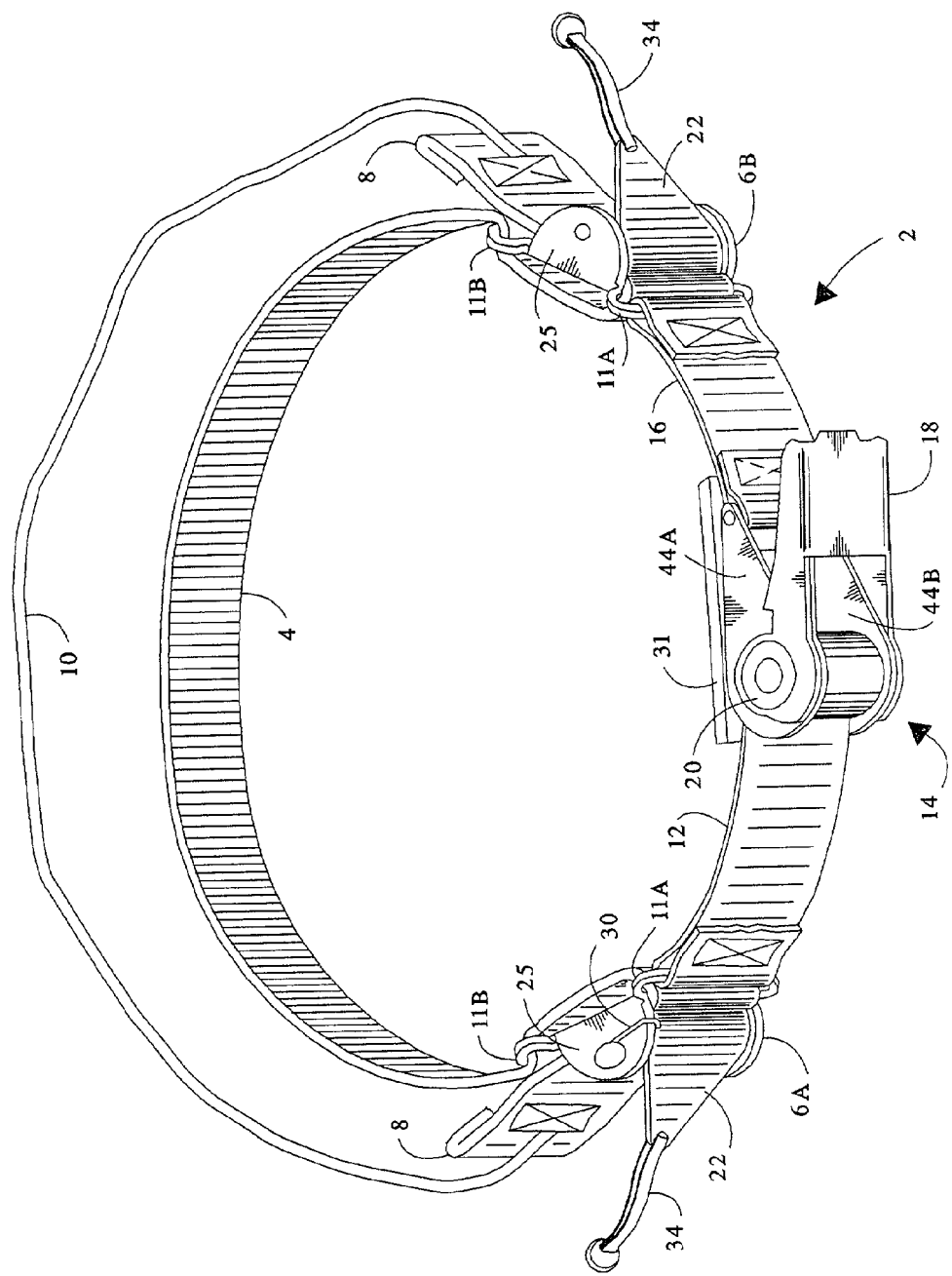
FIG. 1 is a pictorial view of the invention.

Referring to FIGS. 1 through 5, the tourniquet device of this invention as illustrated is generally designated 2. The invention has a first belt 4 having opposite ends 8 which loop back through respective "slip" buckles, 6A and 6B, which are so called because they each allow the belt 4 to easily slip through in one direction, indicated by arrow 7, but prevent movement of the belt through said each in the opposite direction. The first belt functions as one of two adjustable length segments of a tourniquet loop of this invention. A pull cord 10 extends between the first belt's opposite ends, each end of the pull cord being connected to a respective end 8 of the first belt 4. In operation, pulling the cord (in the general direction indicated by arrow 9 in FIG. 7) draws the end portions of the first belt further through respective slip buckles, in directions indicated by the arrows 7, and thereby shortens the segment of the first belt disposed between the slip buckles. Alternatively, the pull cord can be an integral extension of the first belt in which case the first belt would be a complete loop.

Referring again to FIGS. 1 through 5, a second belt 12, which is the second of the two adjustable length segments of the tourniquet loop of this invention, has one end connected to a belt-coupling loop 11A extending from one of the two slip buckles 6A while the second belt's other end is engaged with a belt tightening device, generally designated 14. The belt tightening device 14 preferably includes a cylindrical spool 20 to which the other end of the second belt is affixed for being spooled, a lever 18, and a rachet-action mechanism (not shown) which rotates the spool in a spooling direction whenever a user operates the lever. The lever 18 is operated by reciprocally rotating the lever about the rachet mechanism's axis 19. In operation, a user selectively shortens the free length, i.e. the unspooled length, of the second belt 12 by operating the lever 18 to reel more of the second belt onto the spool 20. The belt tightening device 14 further includes an elongated arm 21 which extends from the rachet mechanism and has a distal end which is connected to a belt-coupling loop 11 extending from the other slip buckle 6B, the connection being preferably by means of a relatively short, fixed-length, third belt 16. In operation, the elongated arm 21 is actually a segment of the tourniquet loop and when the loop is coarsely tightened about a limb, as will be explained further below, the tautness of the loop sufficiently stabilizes the elongated arm 21 to enable it to react against the torque applied to the rachet mechanism by the lever during its operation. The third belt 16 can alternatively be replaced by any other suitable means for connecting the distal end of the elongated arm 21 to the tourniquet loop.

In operation, by pulling the lever 18 away from third belt 16 in the direction indicated by arrow 17, the second belt will be further spooled by one or more ratchet increments depending on the angular stroke of the lever. When the lever is so pulled, a pair of ratchet gears (not shown) at opposite ends of the spool 20 are rotated by the lever, and as the ratchet gears rotate, a pair of spring-biased detents (not shown) ride on the gears' teeth and are urged to seat in the valleys between adjacent teeth to prevent unspooling of the second belt as the lever is reciprocated backward for another pull, i.e., the detent catches keep the belt spooled while allowing the lever to be pushed back to its starting point for additional pulls if desired. As the lever is repeatedly operated in pump fashion, the detents will continue to ride on and catch the ratchet gears' teeth until the unspooled segment of second belt has been shortened to a user selected extent. Preferably the angular stroke of the lever in cooperation with the rachet mechanism allows a user to spool through multiple rachet increments for each pull so that the free segment of the second belt can be rapidly shortened if desired.

Figure 2:
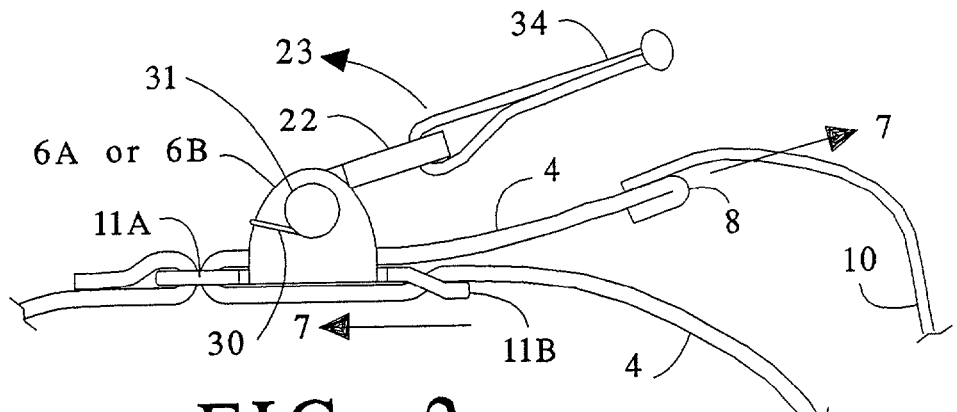
FIG. 2 is a plan view of a preferred slip buckle according to this invention.
Figure 3:
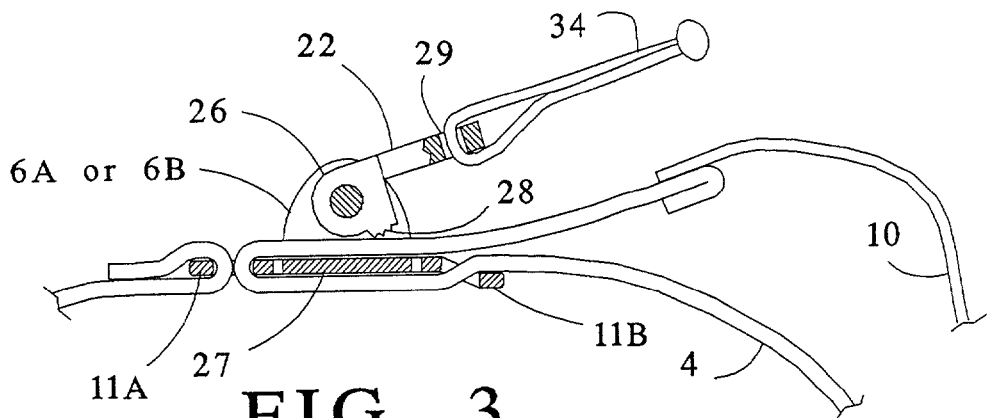
FIG. 3 is a cross-sectional view of the slip buckle of FIG. 2.
Figure 4:
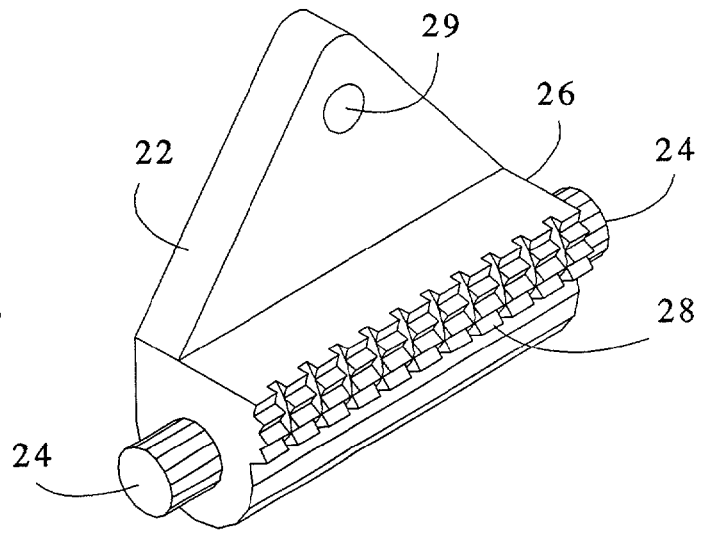
FIG. 4 is a pictorial view of a one-way locking cam which is a part of the slip buckle illustrated in FIGS. 2 and 3.
Figure 6:
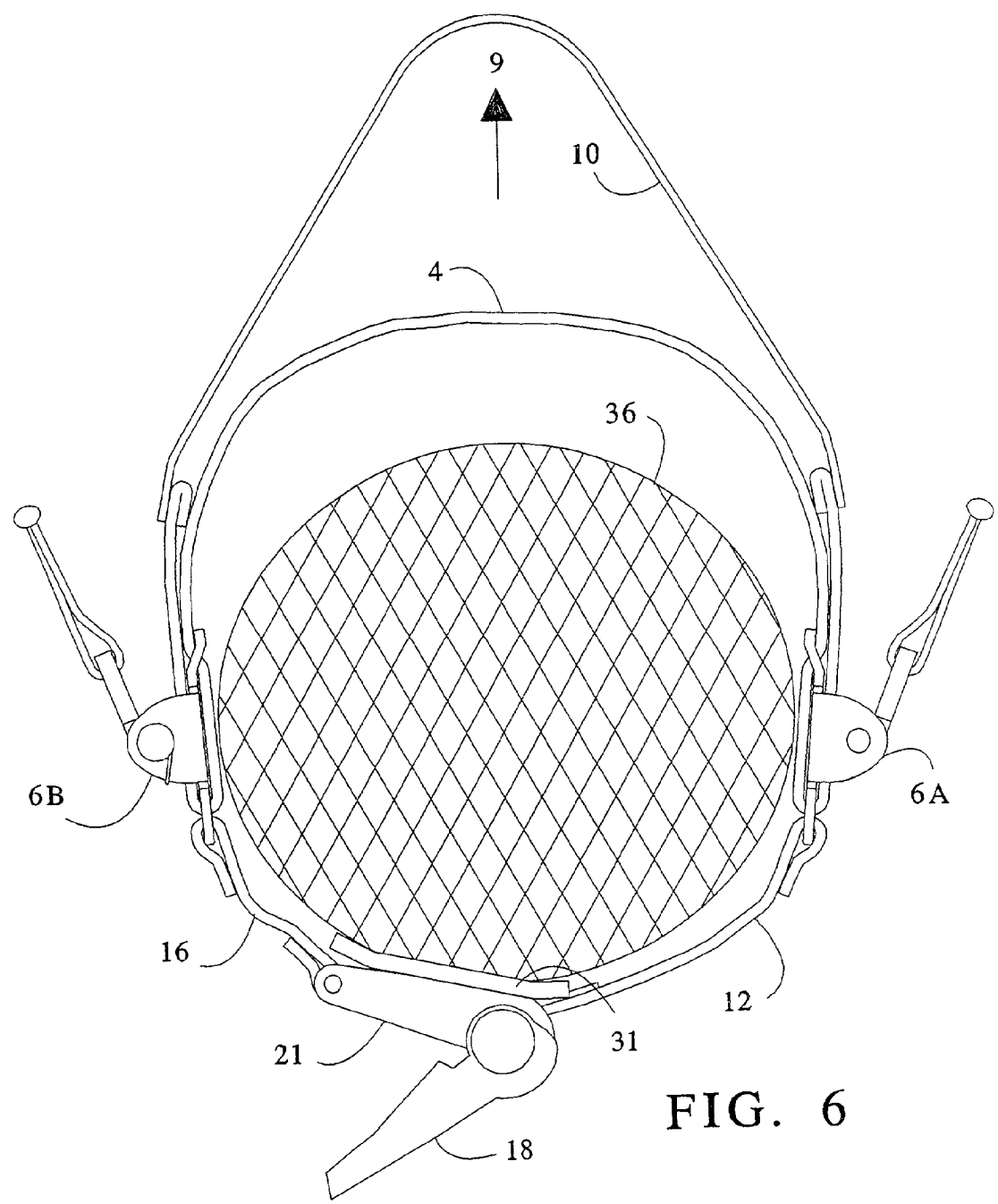
FIG. 6 is a plan view illustrating a first step in tightening the invention about the injured arm. In this view the person has started coarsely tightening the invention about the injured arm by using his or her usable hand (not shown) to pull a tightening cord.

Referring to FIGS. 2–4, each slip buckle has a manually operated, spring-biased, release lever 22 which projects preferably tangentially from an integral cylindrical cam 26 having a longitudinal eccentricity having a ridged surface illustrated here as a plurality of longitudinal rows of teeth 28 projecting outwardly, generally normal to the lever 22. The cam pivots on a pair of integral pintles 24 projecting oppositely from the cam's ends, the pintles being turnable in mating holes defined by lateral (with respect to belt 4) opposing flanges 25 projecting normally from a planar buckle base 27, and extending longitudinally from the buckle base at opposite ends are belt guide loops, 11A and 11B. As best illustrated in FIGS. 2 and 3, a respective end portion of the first belt 4 extends through the guide loop 11B of each slip buckle to pass underneath the buckle's base 27, then extends up through guide loop 11A, then folds back to extend over the buckle base and beyond, out of the slip buckle. For each slip buckle, a coiled spring 30 encircles about one of the buckle's pintles. The spring has one end (not shown) disposed in a pintle hole (not shown) defined in the pintle, and the spring's other end is anchored by the closest flange, and is held in place by a pintle cap 31. The spring biases the angular disposition of the cam so that the cam's eccentricity impinges, i.e. presses against the belt, wedging the belt between the eccentricity's ridged surface and the buckle's base 27. Thus, pulling the first belt 4 in a direction opposite to that of arrow 7 causes the belt to be seized and wedged by the eccentricity, and the belt will not move. Whereas, pulling the belt in the direction of arrows 7 will meet no such resistance. Moreover, pivoting the release lever 22 against the bias, i.e. in the direction indicated by arrow 23, rotates the eccentricity away from the first belt and releases the belt to be moved freely through the slip buckle, allowing the belt to be pulled through the slip buckle in either direction. Preferably, a lanyard 34 is looped through a hole 29 defined proximate the end of the release lever to make it easier to pull the release lever against the bias. By the use of the levers 22, a user can readily expand the length of the first belt's segment of the tourniquet loop to widen the loop prior to application or to quickly release the tourniquet loop.

Referring to FIG. 5, prior to applying this invention to a limb 36, the tourniquet loop is preferably expanded sufficiently to be easily slipped over the limb. Expansion of the loop is preferably done by increasing the tourniquet loop segment lengths of both the first and second belts, 4 and 12, respectively. The belt tightener 14 further includes a release mechanism (not shown) by which a user can release the rachet mechanism and easily unspool the second belt to expand its segment of the tourniquet loop. Expansion of the first belt's segment of the tourniquet loop is accomplished by pulling the release lever 22 of each slip buckle away from the first belt in the direction indicated by arrow 23 (of FIG. 2), and then pulling the first belt through said each slip buckle in a direction opposite to that indicated by arrows 7 (of FIG. 2).

Figure 7:
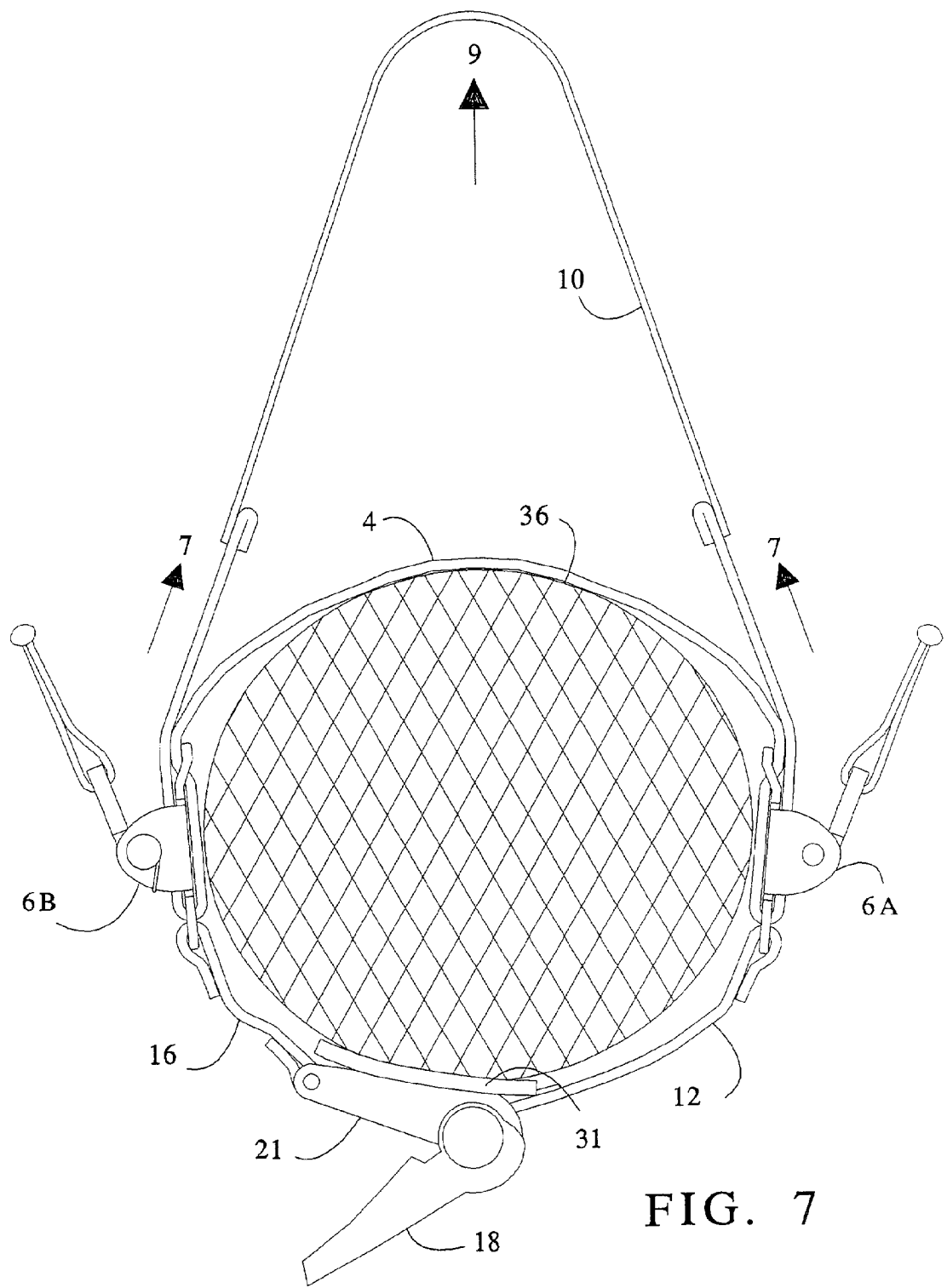
FIG. 7 is a plan view illustrating a second step in tightening the invention about the injured arm. In this view the person has coarsely tightened the invention about the injured arm by further pulling on the tightening cord.
Figure 8:
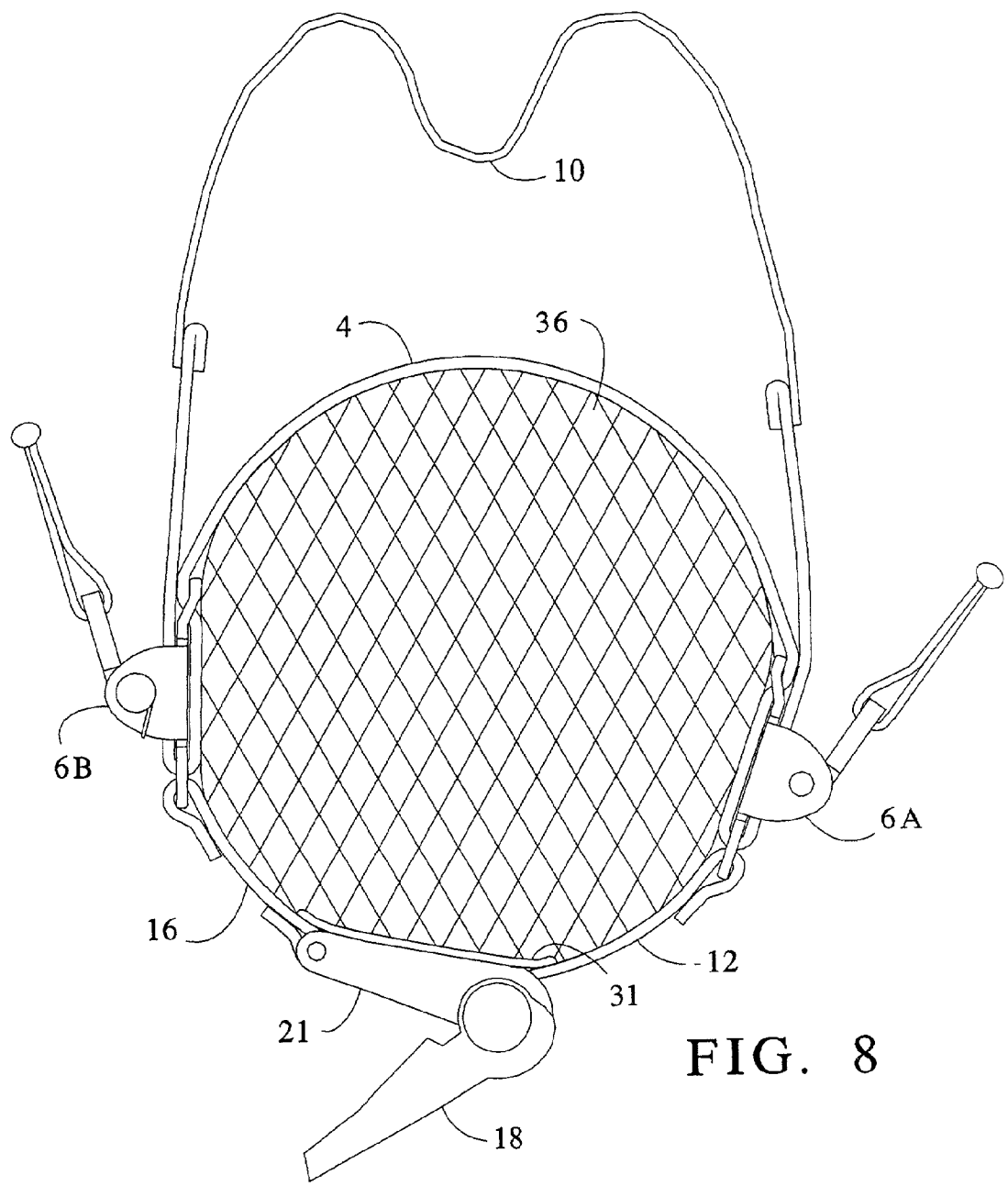
FIG. 8 is a plan view illustrating completion of a third step in tightening the invention about the injured arm. In this view the person has operated the spooling lever to suitably tighten the invention completely around the arm.

Referring to FIGS. 5–8, the preferred operation of this invention is described in terms of self-application. As a first step, a person having a severely bleeding limb 36 slips this invention over the limb so that the tourniquet loop loosely circumscribes the limb, as best illustrated in FIG. 5. Preferably, the tourniquet loop is positioned on the limb to allow easy access to the lever 18 of the tightener 14. Also preferably, a pad 31 is disposed between the limb 36 and the belt tightener 14 to avoid any discomfort which may be caused by the tightener 14 and/or its operation, such as a possible pinching of flesh. Preferably the pad is of resilient material such as compressible foam. After the tourniquet loop loosely circumscribes the limb, the user begins pulling on cord 10 (FIG. 6) in the general direction of arrow 9 to cause the second belt 12, the third belt 16, and/or the arm 21 of the belt tightener 14 to generally abut the limb. Stronger pulling of cord 10 in the direction of arrow 9, as best illustrated in FIG. 7, will result in a significant shortening of the first belt 4 segment of the tourniquet loop until the tourniquet loop is coarsely tightened about the limb. Once the tourniquet loop is coarsely tightened about the limb, the loop is tense enough to sufficiently stabilize the rachet arm 21 to allow a user to operate the belt tightener's lever 18 to finely reel-in the second belt 12 onto the tightener's spool 20 to a point at which a medically appropriate tourniquet has been achieved.

To loosen the invention for removal from a limb, the lanyards 34 can be pulled causing the release levers 22 to release their respective cams' grip on the first belt 4. Pulling on the first belt 4 will pull the first belt through the slip buckles, loosening the device on the arm. Alternately, the rachet mechanism can be released and the second belt unspooled somewhat to temporarily release the tourniquet while keeping the tourniquet coarsely taut enough to reapply the tourniquet by operation of the belt tightener lever.

Referring to FIGS. 9–10, an alternative embodiment is illustrated in which the tourniquet loop can be opened and closed to facilitate use of the device. For example, the loop can be opened to apply it to a limb and then re-closed to tighten it around the limb, preferably by means of a detachable link in the tourniquet loop. Although the detachable link can be disposed anywhere around the tourniquet loop, the preferred embodiment is illustrated as a hook clasp 40 disposed between one of the slip buckles and the belt tightener. The hook clasp is affixed to the end of the belt 16 remote from slip buckle 6B, and can be selectively hooked or unhooked onto a pin 42 extending between the distal ends of opposing elongated plates, 44A and 44B, which form the belt tightener's elongated arm 21.

The foregoing description and drawings were given for illustrative purposes only, it being understood that the invention is not limited to the embodiments disclosed, but is intended to embrace any and all alternatives, equivalents, modifications and rearrangements of elements falling within the scope of the invention. For example the two adjustable length segments of the tourniquet loop of this invention can be alternatively disposed such that the second belt, the spoolable segment, is disposed as a segment of the first belt intermediate the two slip buckles, without departing from the scope of this invention and the claims which follow. Also, one or both of the slip buckles can be integral with the spooling mechanism without departing from the scope of this invention and the claims which follow.

What is claimed is:

1. A tourniquet device configured to be applied to a limb and tightened with a single hand:
    a first tourniquet loop being single-handedly adjustable in length for coarsely tightening the loop around the limb including:
        two opposing slip buckles;
        a first belt extending between and through the slip buckles, each slip buckle allowing the belt to be pulled freely through it in a direction which shortens the length of first belt between the slip buckles but preventing the first belt from traversing through it in the opposite direction; and
        means, gripable by a single hand, for pulling the first belt through the slip buckles in respective directions which shorten the length of first belt between the slip buckles; and
    a second tourniquet loop having a tightening mechanism configured for selectively single-handedly shortening the second tourniquet loop in length for further tightening the loop enough to at least restrict blood flow in the limb.

2. The device according to claim 1 wherein at least one slip buckle further comprises a release which when selectively actuated allows the first belt to be pulled through said at least one slip buckle in either direction.

3. The device according to claim 1 wherein at least one slip buckle further comprises:
    a base;
    a cylinder rotatable on an axis lateral to the first belt, the cylinder including a ridged eccentricity, the cylinder axis being so disposed in fixed relation to the base that the eccentricity can be rotated to impinge upon the first belt which extends between the base and the cylinder and when so rotated the eccentricity seizing and wedging the first belt against the base whenever the first belt is pulled oppositely to the direction which shortens the length of first belt between the slip buckles; and
    a bias which urges the cylinder to assume an angular disposition at which the eccentricity impinges upon the belt.

4. The device according to claim 3 further comprising a lever by which a user can rotate the cylinder against the bias to release the first belt.

5. The device according to claim 1 wherein the second tourniquet loop comprises:
    a second tourniquet loop segment having a first end and a second end affixed at the first end to a first slip buckle;
    a belt tightening mechanism, engaged with the second end of the second tourniquet loop segment, by which a user can selectively shorten the length of second tourniquet loop segment between the belt tightening mechanism and the first slip buckle; and
    a coupling between the belt tightening mechanism and a second slip buckle to complete the tourniquet loop.

6. The device according to claim 5 wherein the belt tightening mechanism further comprises a release for allowing the second belt to loosen.

7. A device for single-handedly applying a tourniquet to a limb comprising:
    two opposing slip buckles;
    a first belt extending between and through the slip buckles, each slip buckle allowing the belt to be pulled freely through it in a direction which shortens the length of first belt between the slip buckles but preventing the first belt from traversing through it in the opposite direction;
    means, gripable by a single hand, for pulling the first belt through the slip buckles in respective directions which shorten the length of first belt between the slip buckles;
    a second belt affixed at one end to one slip buckle;
    a belt tightening mechanism, engaged with the other end of the second belt, by which a user can selectively shorten the length of second belt between the mechanism and said one slip buckle; and
    a coupling between the mechanism and the other slip buckle to complete a tourniquet loop.

8. The device according to claim 7 wherein the tourniquet loop can be opened and closed as needed.

9. The device according to claim 7 further comprising a link in the tourniquet loop which can be selectively opened and closed as needed.

* * * * *